(12) United States Patent
Genger et al.

(10) Patent No.: US 6,626,174 B1
(45) Date of Patent: Sep. 30, 2003

(54) DEVICE FOR ASSESSING THE AIR PRESSURE BEING APPLIED IN AUTOMATIC VENTILATION THROUGH POSITIVE AIRWAY PRESSURE

(75) Inventors: Harald Genger, Starnberg (DE); Peter Drumm, München (DE)

(73) Assignee: Map Medizintechnik fur Arzi und Patient GmbH & Co. KG (DE)

( * ) Notice: Subject to any disclaimer, the term of this patent is extended or adjusted under 35 U.S.C. 154(b) by 0 days.

(21) Appl. No.: 09/830,550
(22) PCT Filed: Oct. 27, 1999
(86) PCT No.: PCT/EP99/08130
§ 371 (c)(1), (2), (4) Date: Jul. 9, 2001
(87) PCT Pub. No.: WO00/24446
PCT Pub. Date: May 4, 2000

(30) Foreign Application Priority Data

Oct. 27, 1998 (DE) .......................................... 198 49 571

(51) Int. Cl.[7] .......................... A61M 16/00; A62B 7/00; F16K 31/02
(52) U.S. Cl. .................. 128/204.21; 128/204
(58) Field of Search .................. ; 128/204.21, 204, 128/203, 204.24; 428/35.7; 261/16; A61B 5/113; A61M 16/00

(56) References Cited

U.S. PATENT DOCUMENTS

| | | |
|---|---|---|
| 4,448,192 A | 5/1984 | Stawticke et al. ...... 128/204.26 |
| 4,457,303 A | 7/1984 | Durkan .................. 128/204.24 |
| 4,542,740 A | 9/1985 | Kleinschmidt et al. 128/204.21 |
| 4,857,369 A | 8/1989 | Oehlenschlaeger et al. ........... 428/35.7 |
| 5,049,317 A | 9/1991 | Kiske et al. .................. 261/16 |
| 5,119,810 A | 6/1992 | Kiske et al. ............ 128/204.26 |

FOREIGN PATENT DOCUMENTS

| | | | |
|---|---|---|---|
| DE | 19701617 A1 | 7/1989 | .......... A61M/16/00 |
| DE | 3906202 A1 | 9/1990 | .......... A61M/16/00 |
| DE | 19746742 A1 | 5/1999 | .......... A61M/16/00 |
| EP | 651971 A1 | 5/1995 | .......... A61B/5/113 |
| EP | 671180 A1 | 9/1995 | .......... A61M/16/00 |
| GB | 2077444 | 12/1981 | .......... A61B/5/08 |
| GB | 0651971 A1 | * 10/1995 | .......... A61B/5/113 |
| WO | WO 95/32016 | 11/1995 | .......... A61M/16/00 |
| WO | WO95/32016 | * 11/1995 | .......... A61M/16/00 |
| WO | WO 97/22377 | 6/1997 | .......... A61M/16/00 |
| WO | WO 98/47554 | 10/1998 | .......... A61M/16/00 |
| WO | WO98/47554 | * 10/1998 | .......... A61M/16/00 |

OTHER PUBLICATIONS

Dtsch. Med. Wsch.r, 122, pp 1482–1488 (1997) English Abstract.
Dtsch. Med. Wschr., 122, pp 789–793 (1997).
Jul. 16, 1999 Office Action from Germany priority application No. 19849571.4.

* cited by examiner

Primary Examiner—Henry Bennett
Assistant Examiner—Sabrina Dagostino
(74) Attorney, Agent, or Firm—Ohlandt, Greeley, Ruggiero & Perle, LLP; George W. Rauchfuss, Jr.

(57) ABSTRACT

The invention relates to a device for assessing the applied air pressure during automatic respiration through positive airway pressure. The air pressure applied is varied by the device according to the invention so that at least three different pressure values can be adjusted. The corresponding respiratory gas flow is measured. On the basis of the relation of the measured respiratory gas flows to each other it is determined whether the applied air pressure is below or above an optimal air pressure or whether the applied air pressure is the optimal air pressure. The device according to the invention can be applied for adjusting the optimal air pressure in respirators used in the CPAP therapy. The device according to the invention provides the advantage of enabling an easy and reliable control of the applied air pressure.

22 Claims, 3 Drawing Sheets

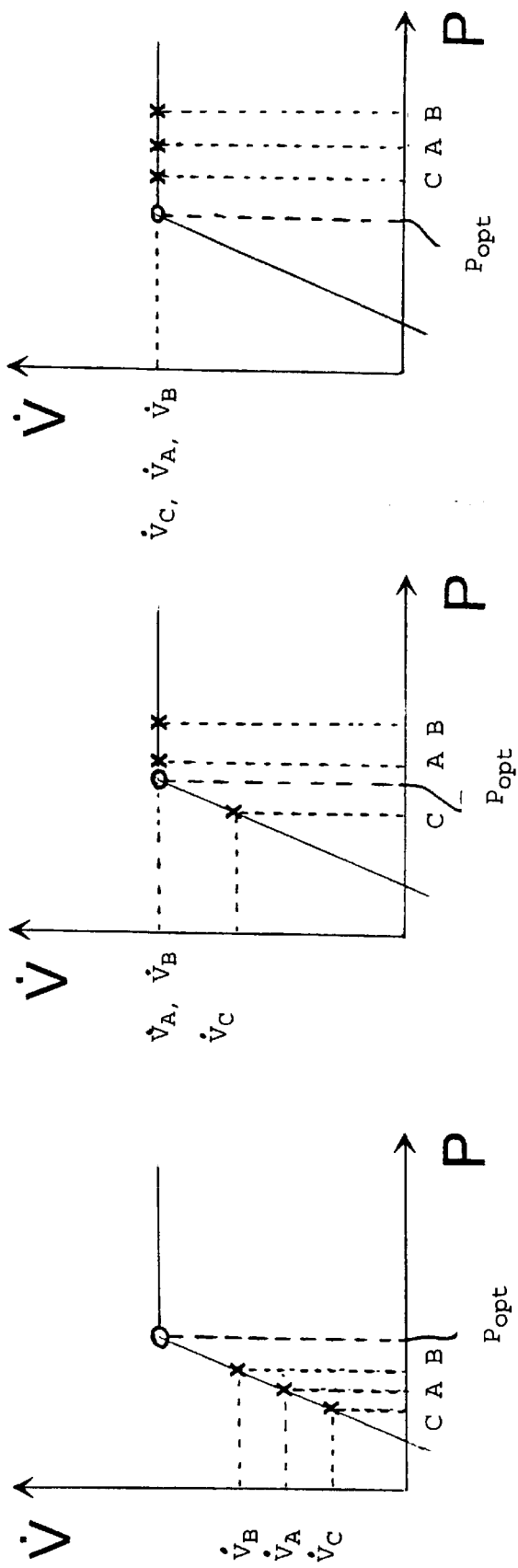

DEVICE FOR ASSESSING THE AIR PRESSURE BEING APPLIED IN AUTOMATIC VENTILATION THROUGH POSITIVE AIRWAY PRESSURE

The invention relates to a device for assessing the applied or exerted air pressure during automatic respiration through positive airway pressure. The device can be used in the CPAP (continuous positive airway pressure) therapy. The CPAP therapy is described in more detail in Chest, vol. 110, pages 1077 to 1088, October 1996 and Sleep, vol. No. 19, pages 184 to 188.

In the CPAP therapy, a patient is supplied, e.g. at night, with a constant positive pressure via a nose mask. This positive pressure should guarantee that the upper airways remain completely open during the entire night and thus no obstructive respiratory disorders occur. Since the required pressure can change at night depending on the sleep stage and the body position, either a variable pressure must be supplied to the patient or the highest pressure which is required at night. It is advantageous if the patient can be supplied with an optimal pressure. An optimal pressure $P_{opt}$, or also effective pressure $P_{effective}$ is the pressure at which the patient is supplied with a normal respiratory flow and an increase in the pressure does not lead to an increase in the respiratory gas flow.

Figure 1:
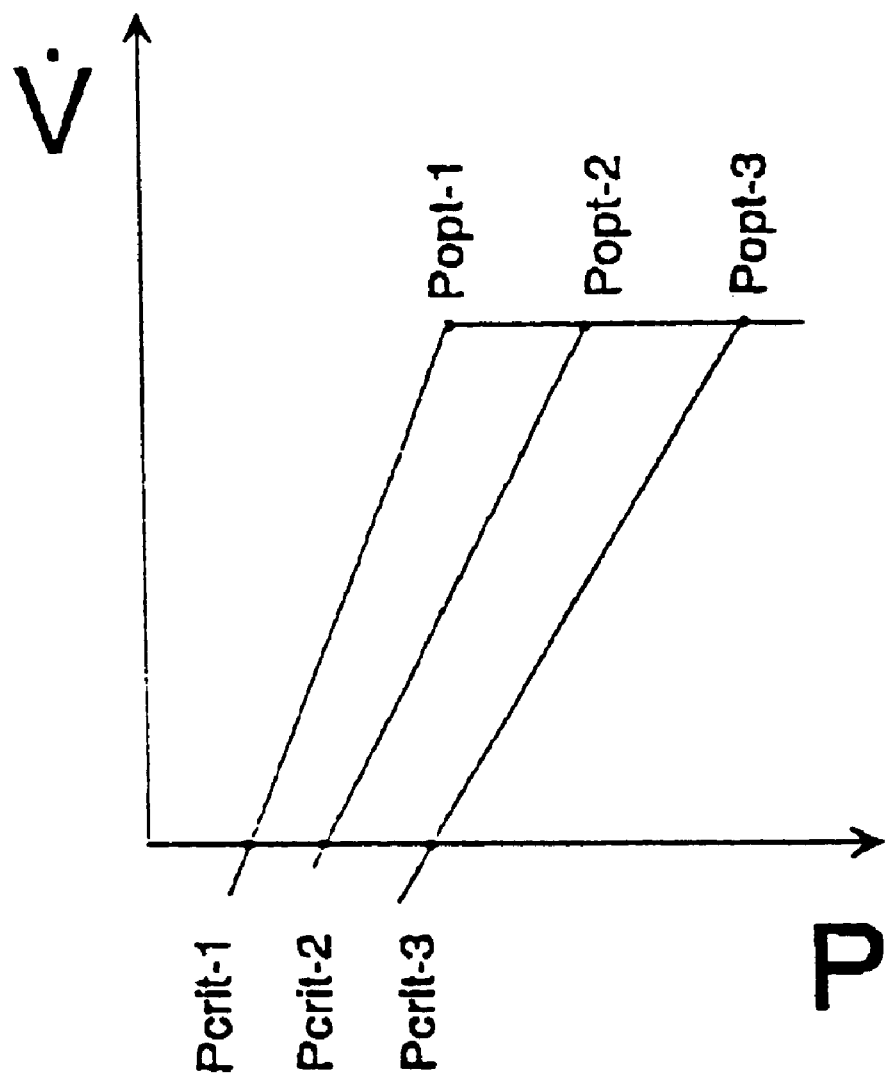

FIG. 1 shows that the optimal air pressure is the kink of the curve of the respiratory gas flow $\dot{V}$ depending on the pressure.

The device according to the invention can be used in the therapy device (AutoSet) in which a maximal respiratory pressure is automatically adjusted. This device is intended for the therapy adjustment in a hospital.

A further application of the device according to the invention is a therapy device (AutoCPAP) in which the air pressure is adjusted to the different requirements of the patient during the night. In this device the optimal pressure is continuously adjusted in accordance with the requirements of the patient. This means that the pressure is increased, maintained or reduced.

In a device with an algorithm for the adjustment or adaptation of the positive air pressure in the CPAP therapy, an initial respiratory pressure can be compared with a threshold value for the respiratory gas flow. In the device the critical pressure $P_{crit}$ and the airway resistance are calculated, and then the desired value of the positive air pressure is controlled such that it is either maintained or changed accordingly.

It is the object of the present invention to provide a device for assessing the applied air pressure during automatic respiration through positive airway pressure by means of which it can be determined whether the applied pressure is the optimal air pressure or deviates therefrom.

For achieving this object, the invention starts out from the basic idea of changing the positive air pressure being applied by means of an adjusting means such that at least three different pressure values can be adjusted, and measuring the respiratory gas flow for the three different pressure values by means of a measuring means. On the basis of the relation of the respiratory gas values to each other, an assessing means assesses whether the applied air pressure lies below or above the optimal air pressure, or whether it is the optimal air pressure.

The invention is advantageous in that already after a few minutes, i.e. without unnecessary discomfort for the patient, it can be determined in which range the applied air pressure lies, so that the air pressure can be adjusted to the optimal air pressure in case of a possible deviation.

Figure 2:
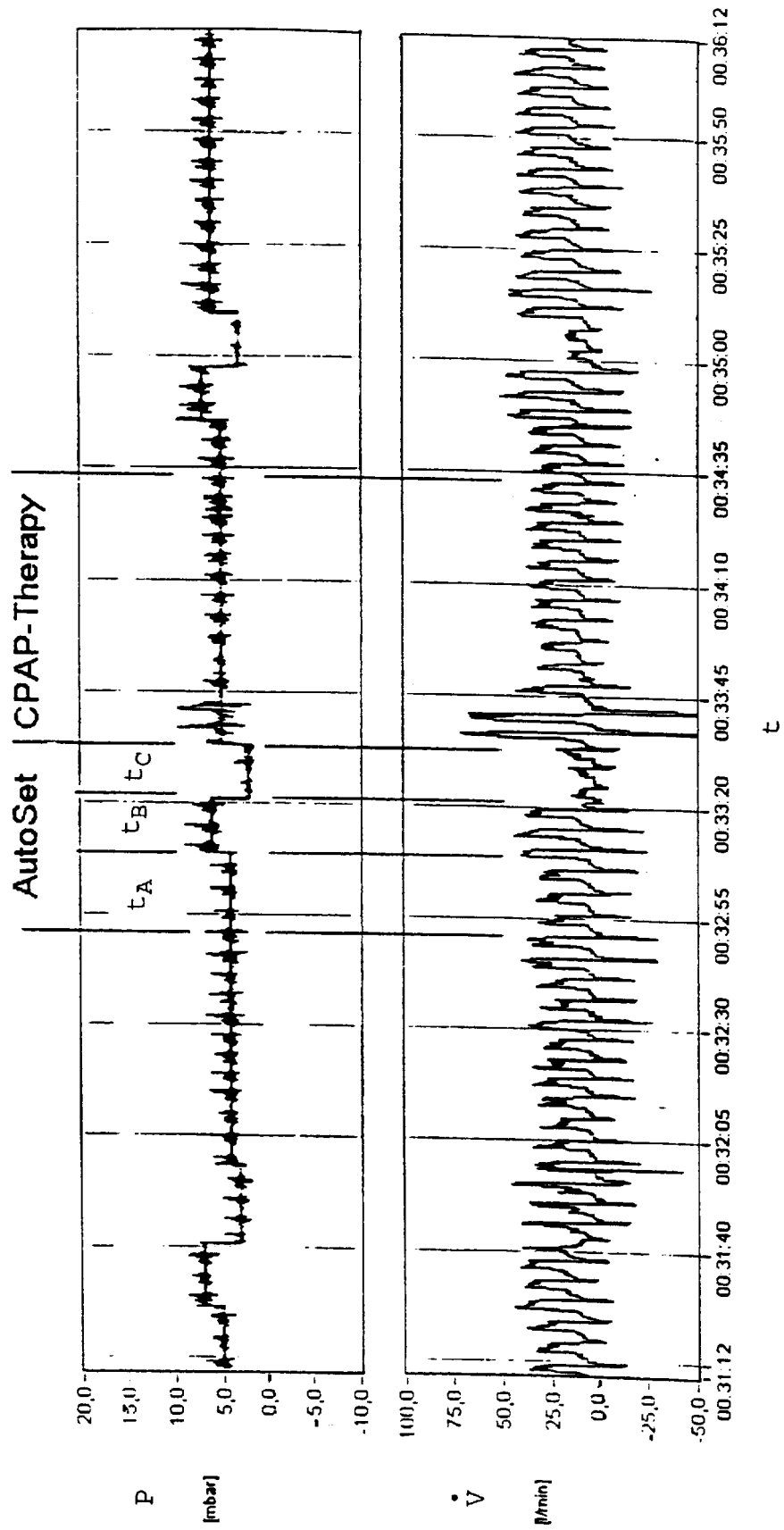

In the following the invention is explained in more detail on the basis of the drawings in which FIG. 1 shows a gas flow/pressure diagram illustrating the change in the gas flow curve during the night, FIG. 2 shows a diagram illustrating the pressure and the gas flow during a diagnosis and therapy phase of the patient, and FIGS. 3a to 3c show gas flow/pressure diagrams with respiratory gas flow values, wherein the gas flow values lie below, within and above the optimal pressure, respectively.

FIG. 1 shows three possible respiratory gas flow curves which can occur at the patient during the night. Depending on the sleep stage and the body position, the critical pressure ($P_{crit-1}$ to $P_{crit-3}$), which prevents the upper airways from closing, can change and lead to different values for the optimal pressure ($P_{opt-1}$ to $P_{opt-3}$). The respiratory gas flow curves can change several times during the night.

By means of a sequence of diagnosis and therapy phases during respiration as shown in FIG. 2, it is permanently assessed with the device according to the invention whether the applied air pressure is the optimal air pressure, i.e. lies in the range around the kinks of the gas flow curves in FIG. 1 or not, and whether the pressure has to be maintained or adapted during the therapy stage. As can be taken from the pressure flow in the upper part of FIG. 2, at the beginning of the diagnosis phase the pressure P is maintained for a predetermined number of breaths and the gas flow $\dot{V}$ (lower part of FIG. 2) is measured, wherein gas flow maxima occur during the inspiration phase. During the same number of breaths as during period $t_A$ the pressure is then increased during period $t_B$, and the gas flow is measured. Then follows period $t_C$ in which the pressure is decreased with respect to the initial pressure (A) and in which during the same number of breaths as in A the gas flow is measured. In the diagnosis phase, which follows the therapy phase, the respiration is continued either with unchanged or increased or decreased pressure in accordance with the results of the diagnosis phase.

In a preferred embodiment of the invention, the maxima of the measured gas flow values are averaged within each diagnosis range, and the gas flow values $\dot{V}_A$ to $\dot{V}_C$ belonging to pressure values A to C, respectively, are determined.

In a first embodiment of the invention the applied air pressure is assessed by classifying the gas flow values in the gas flow/pressure diagram by a comparison of the amounts.

If the following relationship is true $$k \cdot \dot{V}_B > \dot{V}_A \text{ and } k \cdot \dot{V}_A > \dot{V}_C$$

(k<1.0, preferably $0.8 \leq k \leq 0.95$, particularly preferably k=0.9)

the device assesses that the pressure P lies below the optimal pressure $P_{opt}$. This case is shown in FIG. 3a.

If it is true that $$k \cdot \dot{V}_B < \dot{V}_A \text{ and } k \cdot \dot{V}_A < \dot{V}_C$$

the device assesses that the applied pressure P lies above the optimal pressure $P_{opt}$. This case is shown in FIG. 3c.

In all other cases, i.e. if the gas flow values do not correspond to the above conditions, the device assesses that the applied pressure P lies in the range of the optimal pressure $P_{opt}$. Such a case is shown in FIG. 3b. For the gas flow values in this diagram it is true that $k \cdot \dot{V}_B < \dot{V}_A$, however $k \cdot \dot{V}_A > \dot{V}_C$.

This corresponds to the relationships around the optimal pressure in the gas flow/pressure diagram, wherein the gas flow values around the optimal pressure decrease with decreasing pressure.

In a second embodiment of the invention, the maxima of the gas flow in the diagnosis phase are assessed by means of the regression procedure. This procedure is described, e.g., in "Statistik", J. Hartung, Oldenbourgverlag, 8th edition, pages 573 to 581.

A regression straight-line with the parameters $a_{reg}$ (absolute element) and $b_{reg}$ (gradient) is drawn through the quantity of the gas flow maxima. Since the variances of these parameters depend on random errors, the variances can be estimated. The confidence interval for a parameter, which is obtained from the estimated variance, is the range in which the parameter moves with the probability $\gamma$. For assessing whether there is a certain probability for the regression straight-line to have a positive gradient, both limits of the confidence interval for the parameter $b_{reg}$ should be larger than 0 and in case of a negative gradient smaller than 0. If the two interval limits have different signs, no clear statement can made with respect to the gradient of the straight-line.

There are the following cases for assessing the applied pressure during automatic respiration.

Both limits of the confidence interval are >0:

The gas flow maxima lie—with high probability—on a straight-line having a positive gradient, i.e. on the increasing part of the gas flow/pressure diagram. This means that it is assessed that the pressure lies below the optimal pressure.

Both limits of the confidence interval are <0:

If a patient is treated with a too high CPAP pressure, it has been found out that its respiration effort increases and thus the gas flow decreases. If the pressure is decreased, the gas flow will increase again. In case of a straight-line having a negative gradient it is consequently assessed that the applied pressure lies above the optimal pressure.

The limits of the confidence interval have different signs:

Since the straight-line does not have a clear positive or negative gradient, it is assumed that with increasing pressure the gas flow has not changed considerably. A further increase in the pressure would thus not lead to an improved gas flow. It is assessed that the applied pressure is the optimal pressure.

In the following the calculations of the regression straight-line, the estimated value for the error variance of the gradient of the regression straight-line and the confidence interval are indicated.

Determination of the regression straight-line according to the criterion of the smallest square error:

$$Y_{reg}=b_{reg} \cdot X + a_{reg} \text{ with } b_{reg}=\Sigma(X_i-X_{mean})(Y_i-Y_{mean})/\Sigma(X_i-X_{mean})^2 \quad (1)$$

$$a_{reg}=Y_{mean}-b_{reg} \cdot X_{mean}$$

Calculation of the estimated value for the error variance of the gradient of the regression straight-line:

$$s_b^2=s^2/\Sigma(X_i-X_{mean})^2 \text{ with } s^2=1/(n-2) \cdot \Sigma(Y_i-Y_{reg,i})^2 \quad (2)$$

Confidence interval:

$$[b_{reg}-s_b \cdot t_n-2, 1-\gamma/2; b_{reg}+s_b \cdot t_n-2, 1-\gamma/2] \quad (3)$$

$t_n-2, 1-\gamma/2$ table values for $\gamma=0.975$.

The device according to the invention can be used for adjusting the optimal air pressure $P_{opt}$ in a respirator in which a maximally required therapy pressure is adjusted. Such a respirator, which is, e.g., known under the brand name AutoSet, is used in hospitals for therapeutically adjusting a patient. By means of the device according to the invention, the maximal optimal pressure $P_{opt}$, which corresponds to the point $P_{opt-3}$ in FIG. 1, is determined. This point is adjusted by increasing the pressure if the device assesses that the applied pressure lies below the optimal pressure or by maintaining the applied pressure if the device determines that the applied pressure lies in the range of the optimal pressure. In this device the assessment that the applied pressure lies above the optimal pressure does not lead to a decrease in the applied pressure.

The device according to the invention can also be applied in a respirator which is known under the brand name AutoCPAP; this device adapts the therapy pressure during the night to the requirements of the patient and in the course of that also decreases the optimal pressure $P_{opt}$. In this connection also the assessment result of the device that the applied pressure lies above the optimal pressure is used in order to decrease the applied pressure. In FIG. 1 this means that during the night the applied pressure lies between the values $P_{opt-1}$ and $P_{opt-3}$. It is thus guaranteed that the patient is always supplied with sufficient air and that the pressure of the air being supplied is never too high.

For eliminating technical errors, the reaction to the assessment can be delayed by the device according to the invention. This means that it is waited for a plurality of, preferably three equal analysis results before the applied pressure is changed.

For monitoring the state of a patient, e.g. by medical personnel, the assessment result can be made visible on a display, or an acoustic signal can be triggered.

What is claimed is:

1. A device for assessing the applied air pressure (P) during automatic respiration through positive airway pressure comprising
    (a) an adjusting means for varying the applied pressure (P) 50 that at least three different pressure values (A, B, C) can be adjusted,
    (b) al measuring means for measuring the respiratory flow ($\dot{V}$) for the three different pressure values (A, B, C), wherein three corresponding respiratory gas flow values ($V_A$, $V_B$, $V_C$) are obtained, and
    (c) an assessing means for assessing on the basis of the relation of the measured respiratory gas flow values ($\dot{V}_A$, $\dot{V}_B$, $\dot{V}_C$) to each other whether the applied air pressure (P) lies below or above the optimal air pressure ($P_{opt}$) or whether it is the optimal air pressure ($P_{opt}$), and wherein the device is adapted to operate in the following steps:
        (1) measuring the respiratory gas flow ($\dot{V}_A$) by means of the measuring means during a predetermined number of breaths, thereby maintaining the value A,
        (2) increasing the air pressure (P) by means of the adjusting means to the value B and measuring the respiratory gas flow ($\dot{V}_B$) during the same number of breaths: as in step (1), and
        (3) decreasing the air pressure (P) by means of the adjusting means to the value C and measuring the respiratory gas flow ($\dot{V}_C$) during the same number of breaths as in step (1).

2. The device according to claim 1, wherein the assessing means is adapted
    (a) to assess that the pressure (P) lies below the optimal pressure ($P_{opt}$) if it is true that $$k \cdot \dot{V}_B > \dot{V}_A \text{ and } k \cdot \dot{V}_A > \dot{V}_C$$

(b) to assess that the pressure (P) lies above the optimal pressure ($P_{opt}$) if it is true that $$k \cdot \dot{V}_B < \dot{V}_A \text{ and } k \cdot \dot{V}_A < \dot{V}_C$$

(c) and in case of all other values of the respiratory gas flow curve (V), to assess that the pressure (P) is the optimal pressure ($P_{opt}$),
wherein k<1.0, and wherein the pressure values fulfill the following condition: C<A<B.

3. The device according to claim 13 wherein the assessing means assesses the relation of the respiratory gas flow values ($\dot{V}_A, \dot{V}_B, \dot{V}_C$) by means of the regression analysis.

4. The device according to claim 3, wherein the assessing means
   (a) calculates-the regression straight-line on the basis of the respiratory gas flow values ($\dot{V}_A, \dot{V}_B, \dot{V}_C$),
   (b) calculates the confidence interval of the gradient of the regression straight-line at the position of one of the adjusted pressure values (A, B, C),
   ($c_1$) assesses that the pressure (P) lies below the optimal pressure ($P_{opt}$) if both limits of the confidence interval are >0,
   ($c_2$) assesses that the pressure (P) lies above the optimal pressure ($P_{opt}$) if both limits of the confidence interval are <0, and
   ($c_3$) assesses that the pressure (P) is the optimal pressure ($P_{opt}$) if the limits of the confidence interval have different signs.

5. The device according to claim 1, wherein the adjusting means is adapted to adjust 4 mbar as pressure value A, 6 mbar as pressure value B and 2 mbar as pressure value C.

6. The device according to claim 1, wherein the measuring means is adapted to determine the respiratory gas flow ($\dot{V}_A, \dot{V}_B, \dot{V}_C$) by measuring the maxima in the inhalation phase and formation of their arithmetic mean value.

7. The device according to claim 1 for adjusting the optimal air pressure ($P_{opt}$) in a respirator in which a maximally required therapy pressure is adjusted.

8. The device according to claim 7, wherein the pressure (P) is increased if the pressure (P) lies below the optimal pressure ($P_{opt}$), the pressure (P) is maintained if the pressure (P) is the optimal pressure ($P_{opt}$) and the pressure (P) is not decreased if the pressure (P) lies above the optimal pressure ($P_{opt}$).

9. The device according to claim 1 for adjusting the optimal air pressure ($P_{opt}$) in a respirator in which the pressure (P) is adapted to changing requirements of the patient.

10. The device according to claim 9, wherein the applied pressure (P) is increased if the applied pressure (P) lies below the optimal pressure ($P_{opt}$), the pressure (P) is decreased if the applied pressure (P) lies above the optimal pressure ($P_{opt}$), and the pressure (P) is maintained if the applied pressure.(P) is the optimal pressure ($P_{opt}$).

11. The device according to claim 7 wherein a reaction to the result of the device only takes place if a plurality of equal results are obtained.

12. A device for assessing the applied air pressure (P) during automatic respiration through positive airway pressure comprising
    (a) an adjusting means for varying the applied pressure (P) so that at least three different pressure values (A, B, C) can be adjusted, and for adjusting the optimal air pressure ($P_{opt}$) in a respirator in which a maximally required therapy pressure is adjusted,
    (b) a measuring means for measuring the respiratory flow ($\dot{V}$) for the three different pressure values (A, B, C), wherein three corresponding respiratory gas flow values ($V_A, V_B, V_C$) are obtained, and
    (c) an assessing means for assessing on the basis of the relation:of the measured respiratory gas flow values ($\dot{V}_A, \dot{V}_B, \dot{V}_C$) to each other whether the applied air pressure (P) lies below or above the optimal air pressure ($P_{opt}$) or whether it is the optimal air pressure ($P_{opt}$).

13. The device according to claim 12, wherein the assessing means is adapted
    (a) to assess that the pressure (P) lies below the optimal pressure ($P_{opt}$) if it is true that $$k \cdot \dot{V}_B > \dot{V}_A \text{ and } k \cdot \dot{V}_A > \dot{V}_C$$

(b) to assess that the pressure (P) lies above the optimal pressure ($P_{opt}$) if it is true that $$k \cdot \dot{V}_B < \dot{V}_A \text{ and } k \cdot \dot{V}_A < \dot{V}_C$$

(c) and in case of all other values of the respiratory gas flow curve (V), to assess that the pressure (P) is the optimal pressure. ($P_{opt}$),
    wherein k<1.0, and wherein the pressure values fulfill the following condition: C<A<B.

14. The device according to claim 12, wherein the assessing means is adapted to assess the relation of the respiratory gas flow values ($\dot{V}_A, \dot{V}_B, \dot{V}_C$) by means of the regression analysis.

15. The device according to claim 14, wherein the assessing means is adapted
    (a) to calculate the regression straight-line on the basis of the respiratory gas flow values ($\dot{V}_A, \dot{V}_B, \dot{V}_C$),
    (b) to calculate the confidence interval of the gradient of the regression straight-line at the position of one of the adjusted pressure values (A,B, C),
    (ci) to assess that the pressure (P) lies below the optimal pressure ($P_{opt}$) if both limits of the confidence interval are >0,
    (c2) to assess that the pressure (P) lies above the optimal pressure ($P_{opt}$) if both limits of the confidence interval are <0, and
    (c3) to assess that the pressure (P) is the optimal pressure ($P_{opt}$) if the limits of the confidence interval have different signs.

16. The device according to claim 12 which is adapted to operate in the following steps:
    (1) measuring the respiratory gas flow ($\dot{V}_A$) by means of the measuring means during a predetermined number of breaths, thereby maintaining the value A,
    (2) increasing the air pressure (P) by means of the adjusting means to the value B and measuring the respiratory gas flow ($\dot{V}_B$) during the same number of breaths as in step (1), and
    (3) decreasing the air pressure (P) by means of the adjusting means to the value C and measuring the respiratory gas flow ($\dot{V}_C$) during the same number of breaths as in step (1).

17. The device according to claim 12, wherein the adjusting means is adapted to adjust 4 mbar as pressure value A, 6 mbar as pressure value B and 2 mbar as pressure value C.

18. The device according to claim 12, wherein the measuring means is adapted to determine the respiratory gas flow ($\dot{V}_A$, $\dot{V}_B$, $\dot{V}_C$) by measuring the maxima in the inhalation phase and formation of their arithmetic mean value.

19. The device according to claim 12, wherein the pressure (P) is increased if the pressure (P) lies below the optimal pressure ($P_{opt}$), the pressure (P) is maintained if the pressure (P) is the optimal pressure ($P_{opt}$) and the pressure (P) is not decreased if the pressure (P) lies above the optimal pressure ($P_{opt}$).

20. The device according to claim 12 for adjusting the optimal air pressure ($P_{opt}$) in a respirator in which the pressure (P) is adapted to changing requirements of the patient.

21. The device according to claim 20, wherein the applied pressure (P) is increased if the applied pressure (P) lies below the optimal pressure ($P_{opt}$), the pressure (P) is decreased if the applied pressure (P) lies above the optimal pressure ($P_{opt}$), and the pressure (P) is maintained if the applied pressure (P) is the optimal pressure ($P_{opt}$).

22. The device according to claim 12 wherein a reaction to the result of the device only takes place if a plurality of equal results are obtained.

* * * * *